(12) United States Patent
Johnson et al.

(10) Patent No.: US 12,268,424 B2
(45) Date of Patent: Apr. 8, 2025

(54) OSTEOTOMY PLATE, PLATE DRIVER AND METHOD FOR THEIR USE

(71) Applicant: OrthoHelix Surgical Designs, Inc., Medina, OH (US)

(72) Inventors: Jeffrey Johnson, Chesterfield, MO (US); David B. Kay, Akron, OH (US); Jackson R. Heavener, Warsaw, IN (US)

(73) Assignee: STRYKER CORPORATION, Portage, MI (US)

( * ) Notice: Subject to any disclaimer, the term of this patent is extended or adjusted under 35 U.S.C. 154(b) by 0 days.

(21) Appl. No.: 18/521,134

(22) Filed: Nov. 28, 2023

(65) Prior Publication Data
US 2024/0090927 A1 Mar. 21, 2024

Related U.S. Application Data

(60) Continuation of application No. 17/726,709, filed on Apr. 22, 2022, now Pat. No. 11,864,803, which is a continuation of application No. 16/454,119, filed on Jun. 27, 2019, now Pat. No. 11,337,737, which is a continuation of application No. 15/880,952, filed on
(Continued)

(51) Int. Cl.
*A61B 17/80* (2006.01)
*A61B 17/17* (2006.01)
*A61B 17/86* (2006.01)
*A61B 17/92* (2006.01)

(52) U.S. Cl.
CPC ...... *A61B 17/8014* (2013.01); *A61B 17/1728* (2013.01); *A61B 17/1775* (2016.11); *A61B 17/1782* (2016.11); *A61B 17/8052* (2013.01); *A61B 17/8057* (2013.01); *A61B 17/808* (2013.01); *A61B 17/809* (2013.01);
(Continued)

(58) Field of Classification Search
CPC .. A61B 17/8052; A61B 17/8014; A61B 17/80
USPC ........................................................ 606/287
See application file for complete search history.

(56) References Cited

U.S. PATENT DOCUMENTS 4,936,844 A 6/1990 Chandler et al.
5,534,027 A 7/1996 Hodorek
(Continued)

FOREIGN PATENT DOCUMENTS

DE 102007036943.5 A1 2/2009
WO 2009/009057 A1 1/2009

*Primary Examiner* — David W Bates
(74) *Attorney, Agent, or Firm* — DUANE MORRIS LLP

(57) ABSTRACT

An orthopedic plate is specifically configured for use in osteotomies, in which part of the plate extends into a portion of a first bone segment and part is external to the cortical surface of an adjacent bone segment to fix the segments to allow them to fuse. The plate has a first end and a second end where the end which is inserted into the bone has a chamfer and a through hole having a hole axis optionally at an oblique angle to the longitudinal axis of the plate, and which can receive a screw, peg or pin. The second end of the plate includes a locking screw hole and optionally including a compression slot extending in a direction toward a screw hole in the opposing end. Optionally, the non-locking hole has a shroud that forms an arc or portion of a cylinder over the hole. A plate driver having a recess that holds the plate is used to insert the plate into the bone.

21 Claims, 8 Drawing Sheets

Related U.S. Application Data

Jan. 26, 2018, now Pat. No. 10,368,926, which is a continuation of application No. 15/413,968, filed on Jan. 24, 2017, now Pat. No. 9,888,949, which is a division of application No. 14/625,657, filed on Feb. 19, 2015, now Pat. No. 9,572,607, which is a division of application No. 12/803,852, filed on Jul. 8, 2010, now Pat. No. 8,986,353.

(60) Provisional application No. 61/270,486, filed on Jul. 9, 2009.

(52) U.S. Cl.
CPC .......... *A61B 17/8605* (2013.01); *A61B 17/92* (2013.01); *A61B 17/8061* (2013.01)

(56) References Cited

U.S. PATENT DOCUMENTS

| | | |
|---|---|---|
| 5,558,674 A | 9/1996 | Heggeness |
| 5,897,557 A | 4/1999 | Chin et al. |
| 6,203,545 B1 | 3/2001 | Stoffella |
| 6,228,085 B1 | 5/2001 | Theken et al. |
| 6,689,136 B2 | 2/2004 | Stoffella |
| 7,128,744 B2 | 10/2006 | Weaver et al. |
| 7,229,445 B2 | 6/2007 | Hayeck et al. |
| 8,187,276 B1 | 5/2012 | Zahiri et al. |
| 8,231,625 B2 | 7/2012 | Graham et al. |
| 8,652,142 B2 | 2/2014 | Geissler |
| 8,986,353 B2 | 3/2015 | Johnson et al. |
| 10,368,926 B2 | 8/2019 | Johnson et al. |
| 11,337,737 B2 | 5/2022 | Johnson et al. |
| 2003/0153912 A1 | 8/2003 | Graf |
| 2004/0059335 A1 | 3/2004 | Weaver et al. |
| 2004/0116930 A1 | 6/2004 | O'Driscoll |
| 2004/0127908 A1 | 7/2004 | Roman et al. |
| 2005/0070904 A1 | 3/2005 | Gerlach et al. |
| 2005/0107796 A1 | 5/2005 | Gerlach et al. |
| 2005/0171544 A1 | 8/2005 | Falkner |
| 2005/0234454 A1 | 10/2005 | Chin |
| 2006/0058796 A1 | 3/2006 | Hartdegen et al. |
| 2006/0064088 A1 | 3/2006 | Ramare |
| 2006/0149256 A1 | 7/2006 | Wagner et al. |
| 2006/0173459 A1 | 8/2006 | Kay et al. |
| 2007/0016205 A1 | 1/2007 | Beutter et al. |
| 2007/0162018 A1 | 7/2007 | Jensen et al. |
| 2007/0233114 A1 | 10/2007 | Bouman |
| 2007/0276386 A1 | 11/2007 | Gerlach et al. |
| 2008/0015593 A1 | 1/2008 | Pfefferle et al. |
| 2008/0058815 A1 | 3/2008 | Young |
| 2009/0036931 A1* | 2/2009 | Pech ............... A61B 17/7291 606/62 |
| 2009/0088805 A1 | 4/2009 | Leyden et al. |
| 2009/0171399 A1 | 7/2009 | White et al. |
| 2010/0057132 A1* | 3/2010 | Graham ............ A61B 17/8047 606/280 |
| 2010/0131012 A1 | 5/2010 | Ralph et al. |
| 2010/0274293 A1 | 10/2010 | Terrill et al. |
| 2013/0158608 A1 | 6/2013 | Viola |
| 2014/0066995 A1 | 3/2014 | McCormick |
| 2014/0277176 A1 | 9/2014 | Buchanan et al. |
| 2015/0164565 A1 | 6/2015 | Johnson et al. |
| 2017/0056081 A1 | 3/2017 | Langdale et al. |

* cited by examiner

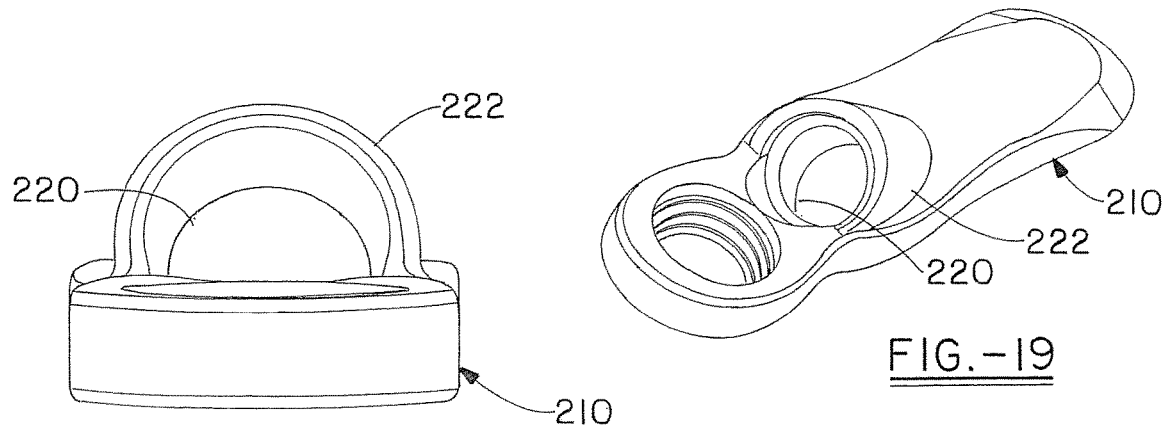
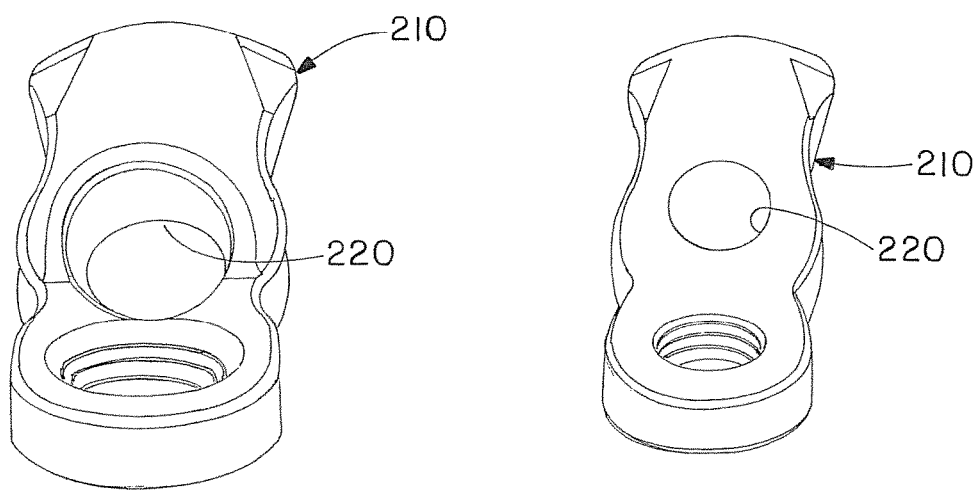
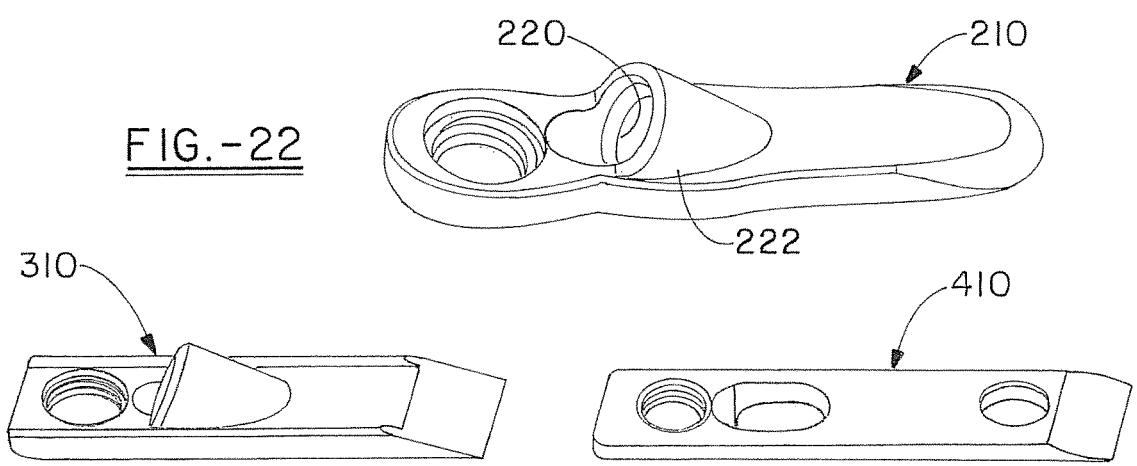

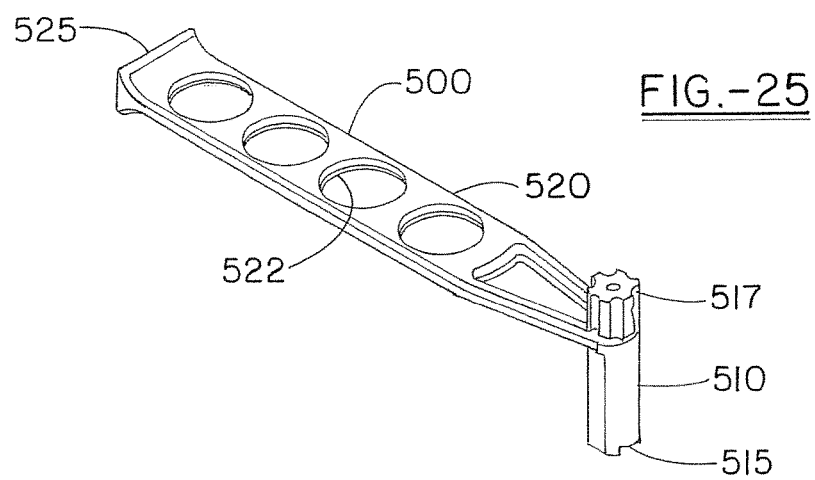
FIG.-25
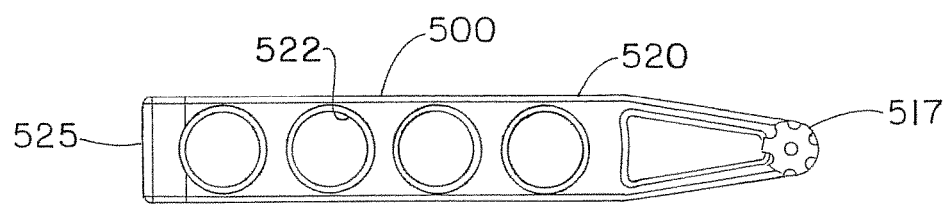
FIG.-26
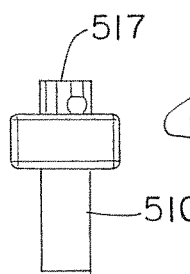
FIG.-29
FIG.-27
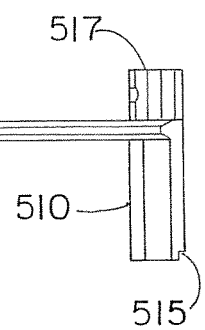
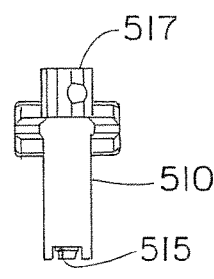
FIG.-30
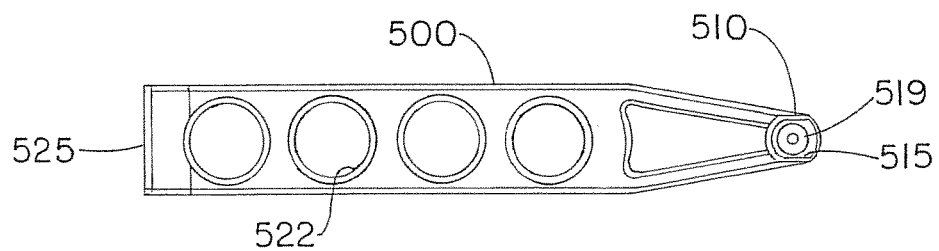
FIG.-28

OSTEOTOMY PLATE, PLATE DRIVER AND METHOD FOR THEIR USE

CROSS-REFERENCE TO RELATED APPLICATIONS

This application is a continuation of U.S. patent application Ser. No. 17/726,709, filed Apr. 22, 2022, which is a continuation of U.S. patent application Ser. No. 16/454,119, filed Jun. 27, 2019 (U.S. Pat. No. 11,337,737), which is a continuation of U.S. patent application Ser. No. 15/880,952, filed Jan. 26, 2018 (U.S. Pat. No. 10,368,926), which is a continuation of patent application Ser. No. 15/413,968, filed Jan. 24, 2017 (U.S. Pat. No. 9,888,949), which is a division of U.S. patent application Ser. No. 14/625,657, filed Feb. 19, 2015 (U.S. Pat. No. 9,572,607), which was a division of U.S. patent application Ser. No. 12/803,852, filed Jul. 8, 2010 (U.S. Pat. No. 8,986,353), which claimed priority to U.S. Provisional Application No. 61/270,486, filed Jul. 9, 2009 the entireties of which are herein incorporated by reference.

FIELD OF THE INVENTION

The present invention relates to an orthopedic plate, which is configured for the fixation of a bone or bones of the foot, hand or wrist in particular following a procedure for fusion of adjacent segments or reconstruction such as various osteotomy procedures. The invention also relates to a surgical driver that is used to implant the osteotomy plate and to a method for the use of the orthopedic plate and associated driver in surgical reconstruction.

BACKGROUND OF THE INVENTION

The feet and the hands both include numerous bones and joints that cooperate together to define quintessential human movement. They are sophisticated, delicate and altogether elegant in function and design. Together the foot and ankle have over 25 bones and 33 joints along with more than 100 named muscles, tendons, and ligaments and a network of blood vessels, nerves, all residing beneath a relatively slim covering of soft tissue and skin. Structurally, the foot has three main anatomical regions: the forefoot, the midfoot, and the hindfoot. These parts work together with the ankle, to provide the body with support, balance, and mobility. A structural flaw or malfunction in any one part can result in the development of problems, which are manifested in other areas of the body. The hand forms a cognate to the foot with 27 bones within the hand and wrist. There are eight small bones within the wrist called the carpals, which join with the radius and the ulna to form the wrist joint. The carpals connect with the five metacarpals to form the palm of the hand, which terminate in the rays (i.e., the thumb and fingers) formed by the phalanges. The three phalanges in each finger are separated by two joints, called interphalangeal joints (IP joints). The one closest to the MCP joint (knuckle) is called the proximal IP joint (PIP joint). The joint near the end of the finger is called the distal IP joint (DIP joint). The thumb only has one IP joint between the two thumb phalanges. The IP joints of the digits also work like hinges when you bend and straighten your fingers and thumb.

Similarly, the forefoot includes the five toes (which are also known as the "phalanges") and their connecting long bones (or "metatarsals"). Several small bones together comprise a phalanx or toe. Four of the five toes have three phalanx bones respectively connected by two joints. The big toe (or "hallux") has two phalanx bones distal and proximal with a joint in between called the interphalangeal joint. The big toe articulates with the head of the first metatarsal at the first metatarsophalangeal joint (the "MTP" joint) and there are two tiny, round bones called sesamoids on the plantar side of the metatarsal head. The phalanges are connected to the metatarsals at the ball of the foot. The forefoot balances pressure on the ball of the foot and bears a substantial amount of the body weight.

The bones of the midfoot from medial to lateral are the $1^{st}$ through $3^{rd}$ cuneiform, the cuboid, and the crescent shaped navicular bone posterior to the cuneiforms, which also forms a joint with the talus that forms the basis for the ankle joint at the hinged intersection of the tibia, the fibula, and the foot. The five tarsal bones of the midfoot act together form a lateral arch and a longitudinal arch which help to absorb shock. The plantar fascia (arch ligament) underlays the bones of the midfoot and along with muscles, forms a connection between the forefoot and the hindfoot. The toes and their associated midfoot bones form the first through fifth rays beginning with the great toe as the first ray. The bones which form the palmate portion of the hand are: the scaphoid, the lunate, the triquetrum, the pisiform, the trapezium, the trapezoid, the capitate, and the hamate, which act in concert to allow the opposition of the thumb with each of the fingers and to permit the uniquely human ability to manipulate objects.

The hindfoot is composed of three joints (subtalar, calcaneocuboid & talonavicular) and links the midfoot to the ankle. The heel bone (or "calcaneus") projects posteriorly to the talus and forms a lever arm to activate the hinged action of the foot so as to allow propulsion of the entire body from this joint. The calcaneus is joined to the talus at the subtalar joint. The mid-foot is often the subject of trauma, such as results from falls, vehicle crashes and dropped objects. These accidents often result in severe fractures and/or dislocations. In addition, there are several conditions which result from congenital deformation or which arise as a result of repeated use type injuries. Surgical intervention that includes surgical sectioning of bone or an "osteotomy" is often used to restructure the bones as a treatment for such conditions. For example, the calcaneal translational osteotomy, with which the present invention might be used, is typically used to treat a condition that is the result of adult acquired flatfoot deformity. The present invention is likewise useful for conditions of the hand that result from prior trauma, surgical intervention or defects from birth or that develop with age (such as rheumatoid arthritis).

Examples of some of the other procedures with which the present invention could be used include hallus valgus and hallus rigidus corrections, and bunionectomies. Other applications which could use the present invention include first and fifth metatarsal chevrons, translational osteotomies, closing wedge osteotomies, pediatric femoral osteotomies, metacarpal and calcaneal rotational osteotomies, intrarticular osteotomies and hand and wrist realignment osteotomies.

Typical surgical treatment of the foot or hand re-establishes a normal anatomy while the fractured bones mend. In some cases, fusion of a joint may be necessary, for example, where arthritis arises in a patient due to use injuries, poor bone or prior unsuccessful surgeries. One current surgical treatment of these conditions requires that pins, wires and/or screws be inserted to stabilize the bones and joints and hold them in place until healing is complete. For example, a pin or screw may be introduced medially into the internal cuneiform and through the base of the second metatarsal bone. While the use of k-wires, pins, and screws may provide acceptable results for younger and more plastic patients, these methods of fixation are not always satisfactory.

SUMMARY OF THE INVENTION

In accordance with the present invention an orthopedic plate (as well as a driver for the plate) is provided which can be used to good advantage in an osteotomy. In a first embodiment, the plate has a footprint that is a modified rectangle having a first end with rounded corners, and a longitudinally opposing end with a cutting edge that may include a taper or a crescent shape. Either two or three of the four sides of the plate, including both long sides and optionally the proximal end have a raised edge or rails which acts to stabilize the plate, and which is connected with a thinner flat web of material that includes one or more holes for screws or pins. At the cutting end, the rails may terminate in pointed insertion tips which are joined by the web that also includes a tapered cutting surface or the plate may simply include the tapered cutting edge. In a second embodiment, the plate has a simple bar-like footprint with a first end tab and a second end tab extending along the longitudinal axis of the plate and with narrowed waist sections between the tabs. At the first end tab, the plate includes a first portion that is inserted into cancellous bone. This portion includes a rounded or tapered chamfered edge that promotes insertion into the bone. At the second end tab, the opposing portion includes a through hole so that the plate can be fixed to an extramedullary portion of an adjacent bone segment. Optionally, the plate includes a compression or translation slot that extends in a direction and causes compression toward a through hole in the opposing cancellous tab. The width of the plate decreases between the holes to allow for bending if desired. In other embodiments, the footprint may by more "organic" in shape, with a rounded tapered insertion surface, a mid-section that flares to accommodate an angled screw hole and a rounded rear section that includes a second perpendicular screw hole. In a further modification of this plate, the plate advantageously includes an angled hole with a shroud that protects the soft tissue from the head of the screw and which aids in optimal compression of the posterior fragment for certain procedures.

The invention can be used in a variety of indications including for example, calcaneal osteotomies Dwyer osteotomy, cotton osteotomy, isolated TMT fusion, Navicular fracture, Evans osteotomy and metacarpal rotational osteotomies, or intrarticular osteotomies or hand and wrist realignment osteotomies. Other applications which could use the present invention include first and fifth metatarsal chevrons, translational osteotomies, and closing wedge osteotomies.

BRIEF DESCRIPTION OF THE DRAWINGS

FIG. 18 is an end view of the plate shown in FIG. 17;
FIG. 19 is a top perspective of the plate shown in FIG. 16;
FIG. 20 is an end perspective of the plate shown in FIG. 16;
FIG. 21 is a bottom perspective of the plate shown in FIG. 16;
FIG. 22 is a side perspective of the plate shown in FIG. 16;
FIG. 23 is a side perspective of the fourth embodiment of the orthopedic plate of the present invention;
FIG. 24 is a side perspective of the fifth embodiment of the orthopedic plate of the present invention;
FIG. 25 is a side perspective of the plate driver of the present invention;
FIG. 26 is a top view of the plate driver shown in FIG. 25;
FIG. 27 is a side view of the plate driver shown in FIG. 25;
FIG. 28 is a bottom view of the plate driver shown in FIG. 26;
FIG. 29 is a first end view of the plate driver shown in FIG. 25;
FIG. 30 is a second end view of the plate driver shown in FIG. 25.

DETAILED DESCRIPTION OF THE INVENTION

Figure 1A:
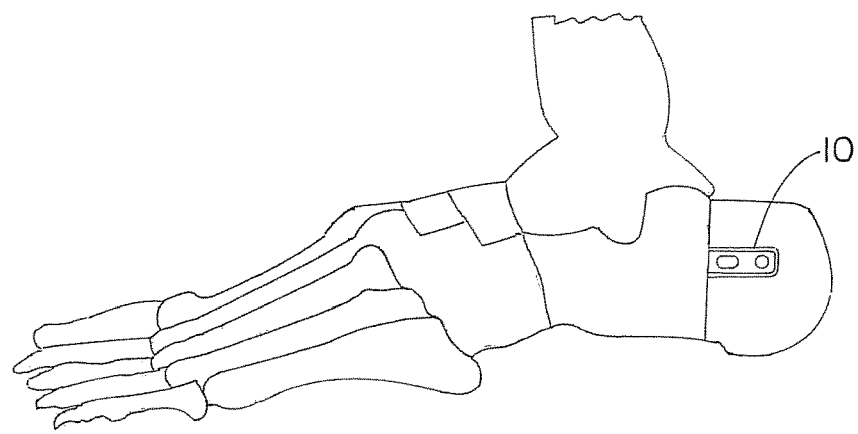
FIG. 1a is a medial view of a foot with an orthopedic plate in accordance with a first embodiment of the invention positioned for use in a translational calcaneal osteotomy procedure.
Figure 1B:
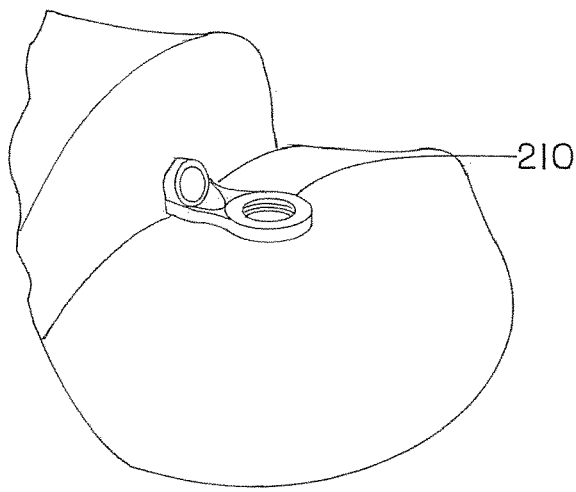
FIG. 1b is a medial posterior view of a foot with a further embodiment of the plate of the present invention also for use in a translational calcaneal osteotomy procedure.

FIG. 1 shows a skeletal version of a foot from the lateral side with a particularly preferred embodiment of the plate 210 of the present invention in place between the junction of the talus and the calcaneus with an angled screw inserted into the Sustentaculum Tali. Thus, FIG. 1 illustrates the plate used in a translational osteotomy of the calcaneus for treatment of flatfoot syndrome. Similarly, it can be used for fixation of other bone segments following osteotomies as previously mentioned.

Figure 2:
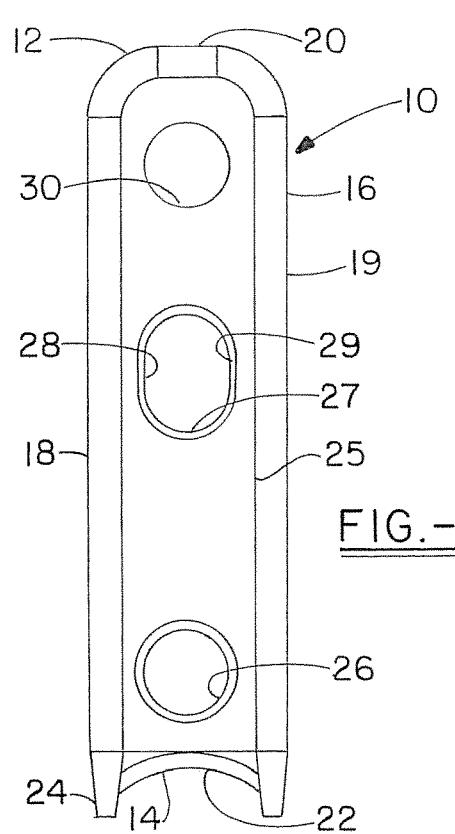
FIG. 2 is a top view of the orthopedic plate of FIG. 1.

As viewed from the top in FIG. 2, it can be seen that the first embodiment of the plate 10 has a rectangular shape with a first end 12 and an opposing cutting end 14 aligned along the longitudinal axis of the plate. The peripheral edges 16 of the plate are raised on three sides, including the two long sides 18, 19 and the squared short wall 20. These edges form rails that help to provide stability for the plate and in particular to inhibit torsion of the plate during insertion and during the recuperation period in which the injury fuses. The rails are rounded at the corners of the squared short wall 20. The opposing short wall includes a chamfered cutting surface 22, which is illustrated as a crescent shape between the two forward extending insertion tips 24 that are coextensive with the long wall edges. The body of the plate is formed by a thinner flat web 25 that extends between the raised edges and includes a number of openings. Preferably, the web 25 includes a first opening 26, or hole in the portion of the plate which extends into the bone and which accepts a screw or a pin in order to help hold the plate in place and to keep it from rotating within the bone. Rearward of that, and somewhere beyond halfway along the long axis of the plate, the plate includes a compression slot 27 that accepts a screw to cause compression toward the first opening. Typically, the compression slot includes a shoulder 28 along its internal edge 29 that slopes in the direction that compression occurs. In the rearward portion, toward the squared end, the plate includes a locking hole 30 which includes a mechanism to cause locking, such as internal threads that mate with external threads on the head of a locking screw to lock this portion of the plate to the extramedullulary portion of an adjacent bone fragment.

In a second embodiment, the plate 110 has a simple bar-like profile that is comprised of a first end with a tab and a second end with a longer tab. The longer tab 112 has a rounded end at its proximal end that necks in slightly into the body of the first tab 112, and the rounded end includes a deep chamfer 115 which tapers from the lateral edge of the plate to an optional through hole 116 which can receive a screw or pin that helps to secure the plate in the cancellous portion of the bone against rotation or movement. The longer tab also includes an obround translation or compression slot 120 at the distal end of the first tab. The plate width flairs slightly around the slot to preserve the metal which defines the slot (preferably to reinforce the slot to inhibit deformation of the slot during any option bending procedures, or even during insertion. Again the plate necks in slightly at the transition between the first tab and the second tab and the distal most 114 of the pair of tabs includes a screw hole 122 (which preferably includes locking means such as internal threads or a variable locking mechanism, so as to form a locking interface between the plate and the respective bone or bone fragment by means of the rigid fastening of the screw in the screw hole in the plate.) The locking hole optionally further includes keyways for a drill guide. The compression slot is configured so as to cause compression along the longitudinal axis of the plate in the direction of the locking screw hole. The plate includes incurvatures 123 between the openings to form waist sections that minimize the material used and maximizes the fit of the plate, as well as allowing additional contouring of the plate in these areas, should it be desired.

In a third embodiment, the plate 210 corresponds in shape and function to the second embodiment. Specifically it has a first rounded tab end having a deep chamfer that permits the plate to be inserted into bone and a second rounded end having a threaded locking screw hole. In this embodiment, the compression slot is replaced by an angled non-locking screw hole 220 which includes a hole shroud 222 forming an arc or a portion of a cylinder raised above the top surface of the body of the plate in order to sufficiently support the screw that is received in this hole and to shroud the head of the screw to help minimize the possibility of soft tissue irritation that the screw head might otherwise provide. The shroud also provides some support and compression within the bone into which it projects. The non-locking hole is angled so that the axis of the screw forms an angle of about 10° to about 45°, and preferably about 15° to about 40°, and more preferably about 25° to about 35° to the longitudinal axis and the hole allows for about 30°, preferably about 20°, and most preferably about 15° of conical rotation of the screw within the screw hole of the plate which is provided to enable the surgeon to capture the sustentaculum. This screw is intended to capture the anterior portion of the calcaneus in a calcaneal osteotomy.

Figure 3:
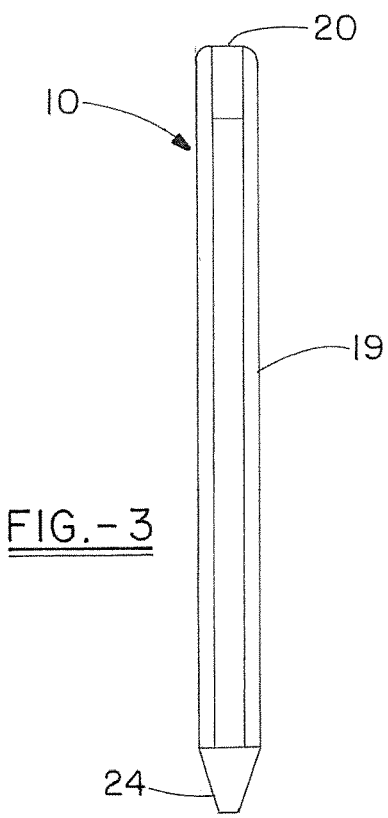
FIG. 3 is a side view of the plate shown in FIG. 2.
Figure 4:
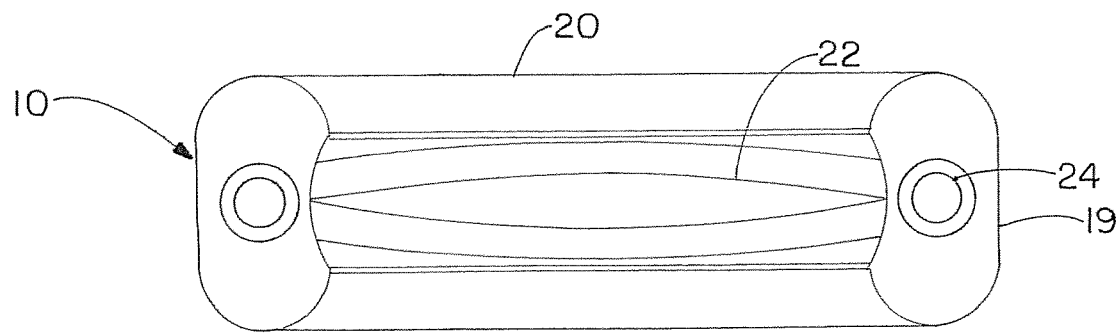
FIG. 4 is an end view of the plate shown in FIG. 3.
Figure 5:
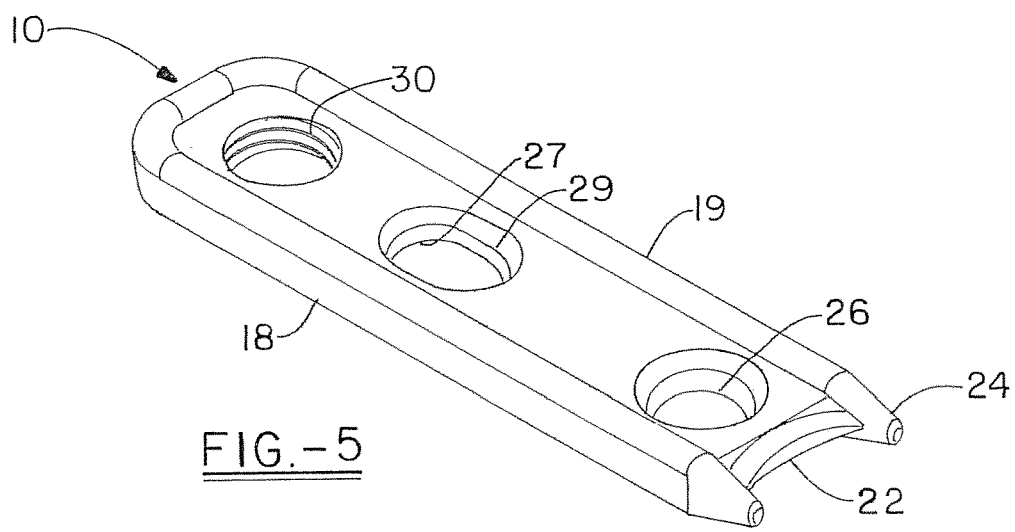
FIG. 5 is a top perspective of the plate shown in FIG. 2.
Figure 6:
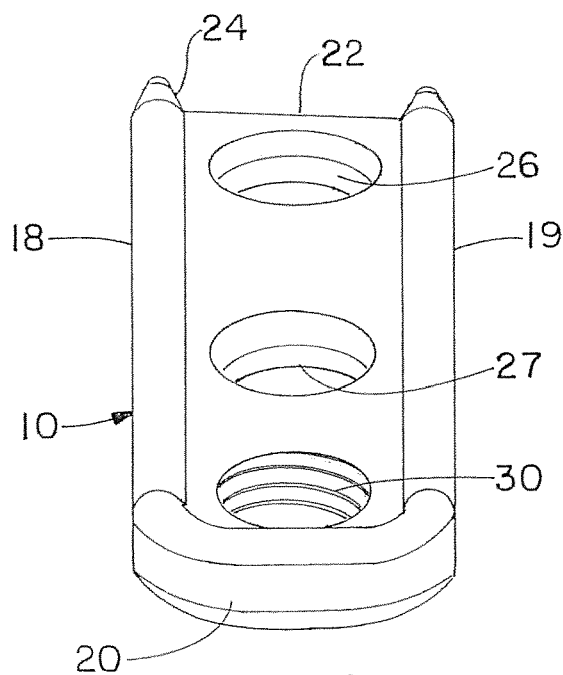
FIG. 6 is an end perspective of the plate shown in FIG. 2.
Figure 7:
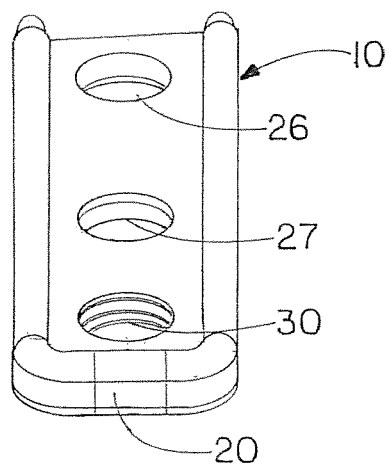
FIG. 7 is a bottom perspective of the plate shown in FIG. 2.
Figure 8:
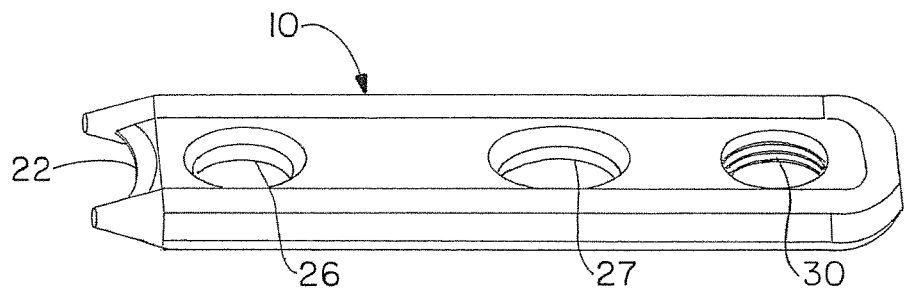
FIG. 8 is a side perspective of the plate shown in FIG. 2.
Figure 9:
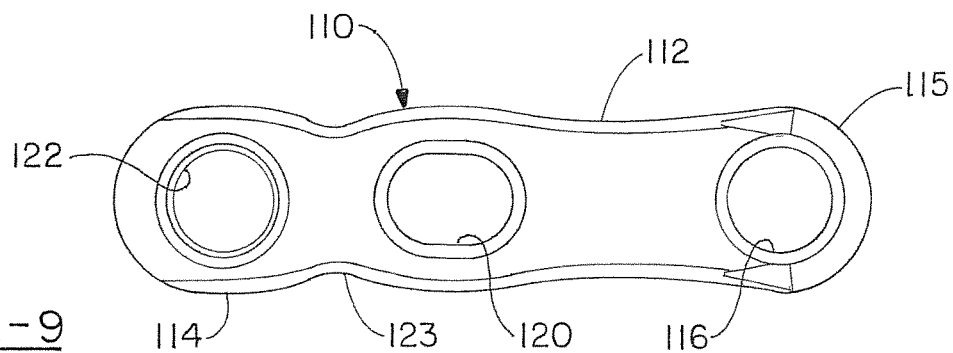
FIG. 9 is a top view of a second embodiment of the orthopedic plate of the present invention.
Figure 10:
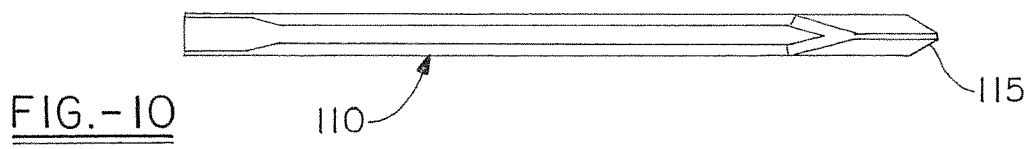
FIG. 10 is a side view of the plate shown in FIG. 9.
Figure 11:
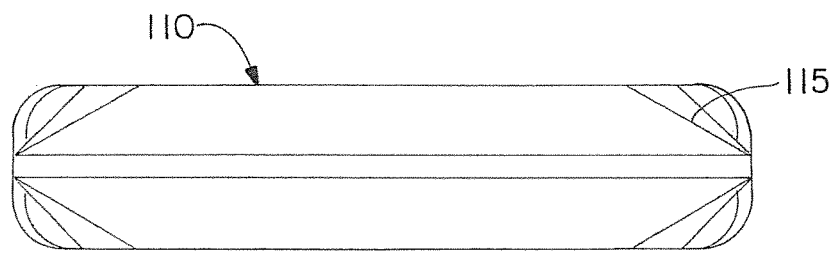
FIG. 11 is an end view of the plate shown in FIG. 10.
Figure 12:
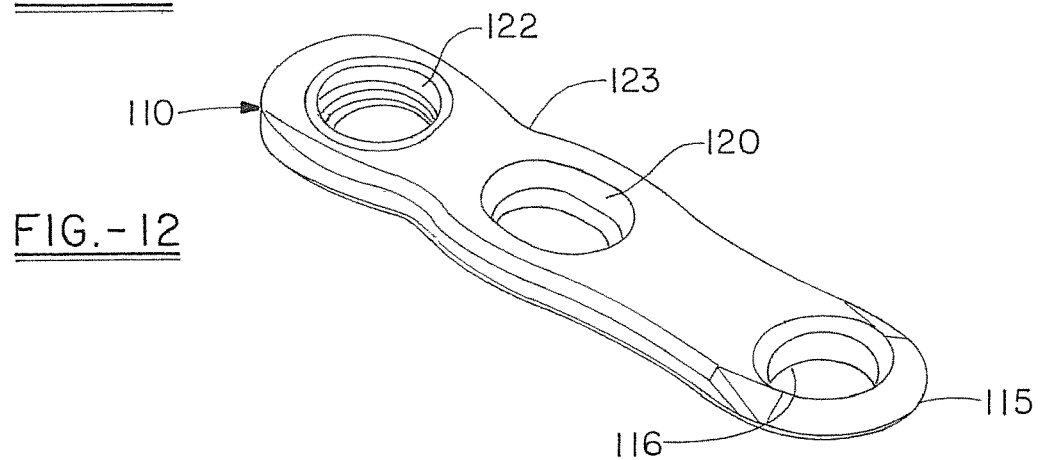
FIG. 12 is a top perspective of the plate shown in FIG. 9.
Figure 13:
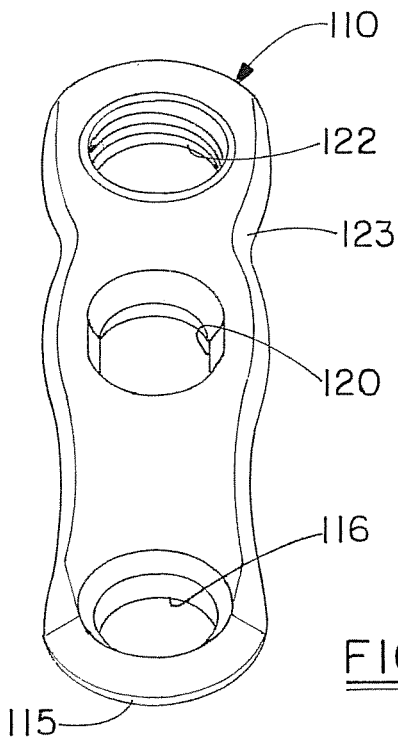
FIG. 13 is an end perspective of the plate shown in FIG. 9.
Figure 14:
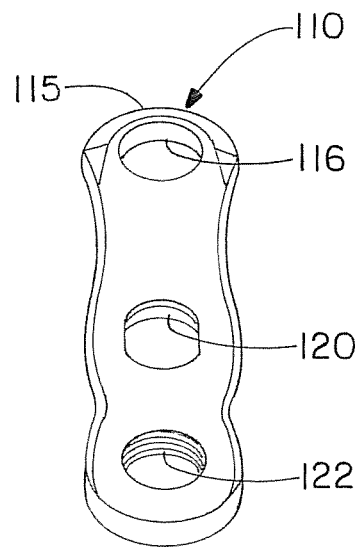
FIG. 14 is a bottom perspective of the plate shown in FIG. 9.
Figure 15:
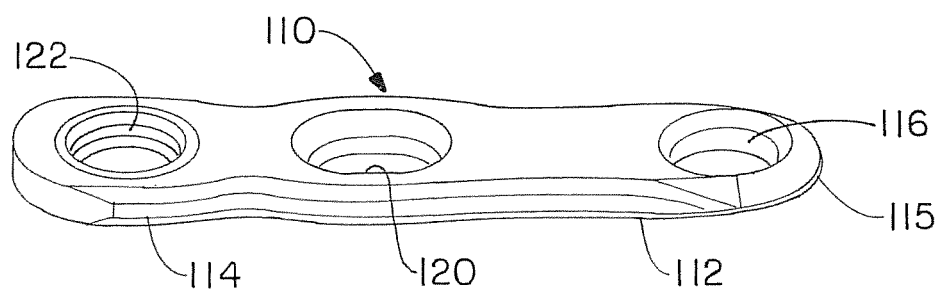
FIG. 15 is a side perspective of the plate shown in FIG. 9.
Figure 16:
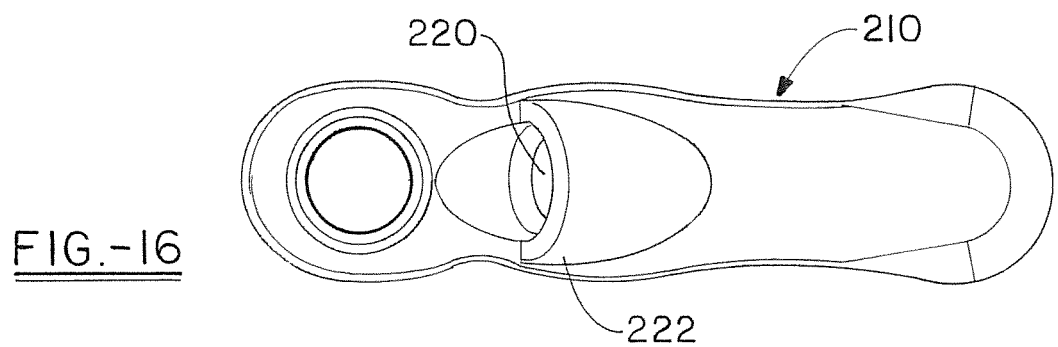
FIG. 16 is a top view of a third embodiment of the orthopedic plate of the present invention.
Figure 17:
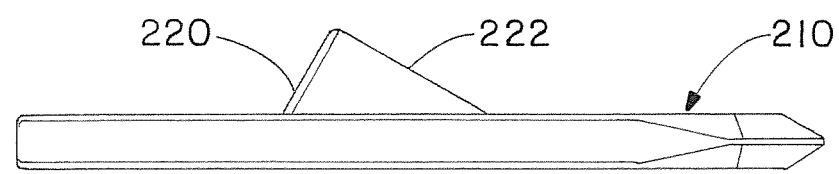
FIG. 17 is a side view of the plate shown in FIG. 16.

FIGS. 3 and 4 illustrate the edge on views of the first embodiment of the plate in along a first length and along the second shorter length, which is perpendicular to the first length. As can be seen the web of the plate has a generally uniform thickness between the inward surface 27 which opposes and optimally, but not necessarily engages the bones, and the outward surface 29. Similarly, the second embodiment is illustrated in edge on views in FIGS. 10 and 11 in which it can be seen that this embodiment that the plate is flat and of a uniform thickness between the bone-facing surface of the cortical portion of the plate. Optionally, the inward surface 127 of the plate 110 could includes a generally uniform radius of curvature along the longitudinal axis so that the plate would have the shape of a segment of a cylinder which maximizes the ability to place the plate as desired without the need for additional pre-surgical contouring for certain applications, although the plate thickness allows for bending if necessary Also optionally for this design, the distal edge of the plate can be of a larger radius or thicker width to provide a broader shoulder 136 so that the proximal portion of the plate can be driven into the bone.

FIGS. 23 and 24 illustrate other embodiments 310, 410 of the orthopedic plate of the present invention that illustrate how different features of the previous embodiments could be combined, including the straight taper cutting edge, and with the compression slot or with the angled screw hole and shroud.

Figure 31:
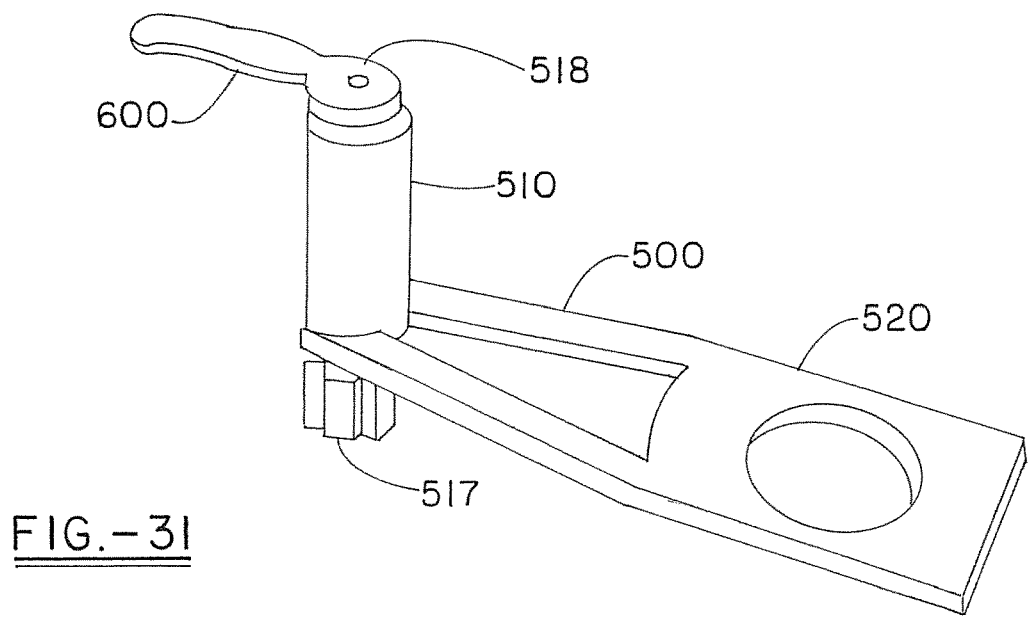
FIG. 31 is a bottom perspective of the plate loosely attached to the plate driver in accordance with the invention.
Figure 32:
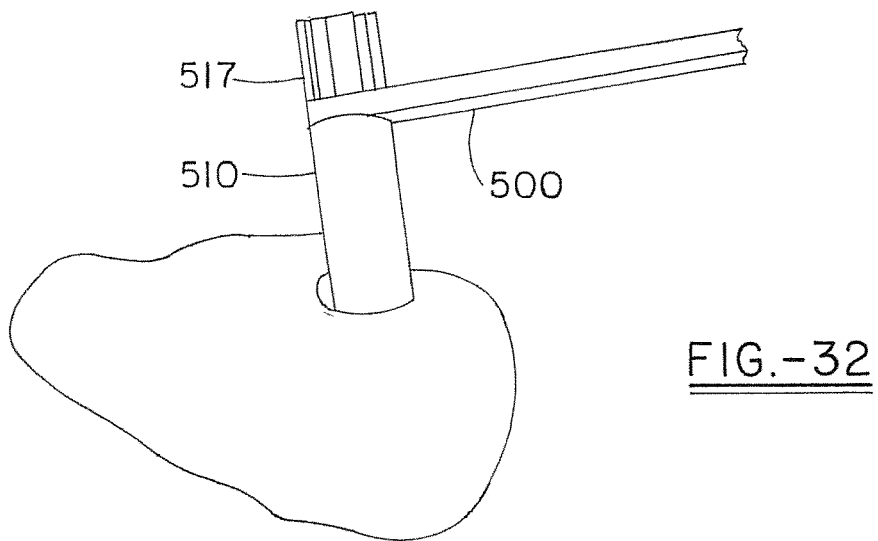
FIG. 32 is a side view of the plate and driver in accordance with the invention during insertion.
Figure 33:
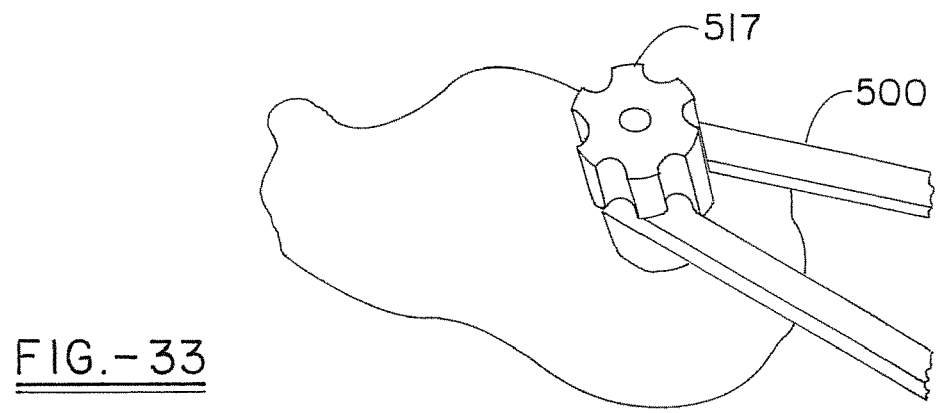
FIG. 33 is a side view of the plate and driver in accordance with the invention during insertion.
Figures 34, 35, 36:
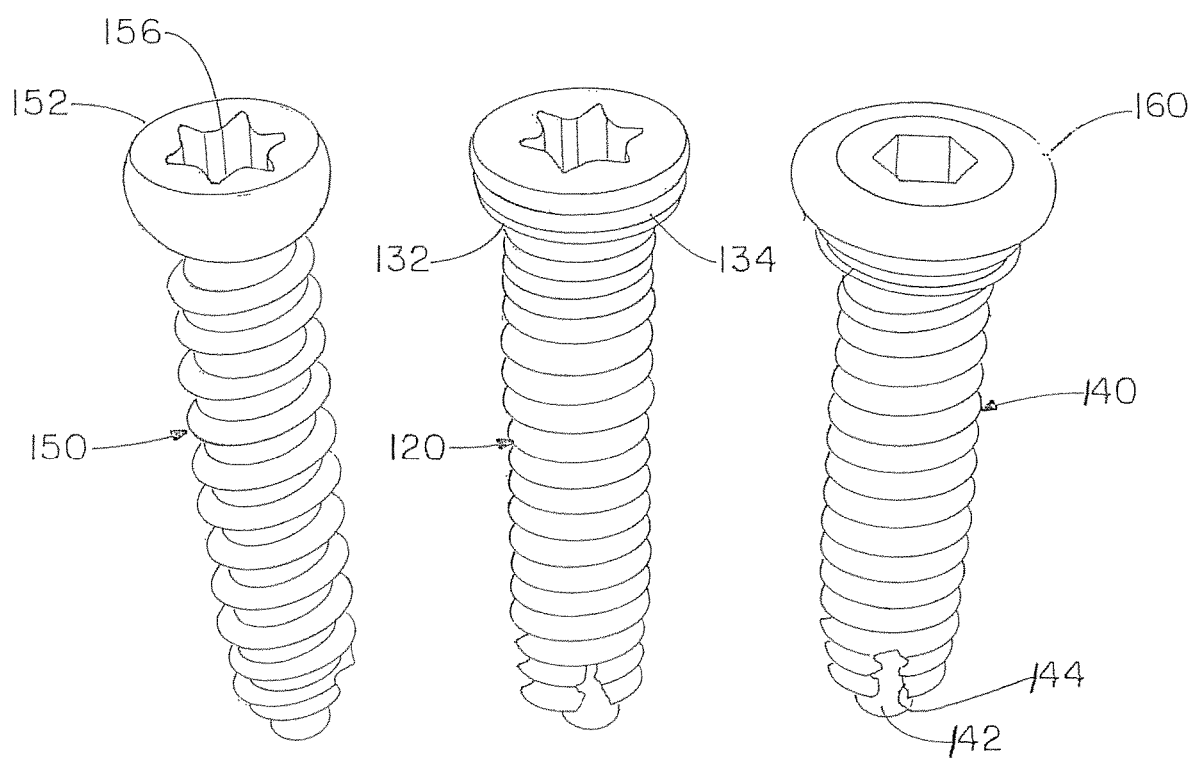
FIG. 34 is a side view of a non-locking screw in accordance with the invention.
FIG. 35 is a side view of a locking screw in accordance with the invention.
FIG. 36 is a side view of a variable locking screw in accordance with the invention.

FIGS. 25 through 30 illustrate the plate driver 500 of the present invention. The driver 500 includes a plate holder portion 510, which has at one end a recess or pocket 515 that captures the end of the plate 600 (see FIG. 31) having the locking hole. Specifically, the plate holder 510 includes a knob 517 joined to a shaft 518 that is journaled within a bore 519 in the plate holder 510. The end of the shaft 518 includes threads that can engage the internal threads of the locking hole in the plate to hole the plate within the plate holder as well as relative to the plate driver. The plate driver further includes a handle 520 that allows the surgeon to hold the plate driver. The plate holder portion holds the plate with the long axis in line with the long axis of the handle, but offset from the plate which gives the surgeon better visibility to the surgical site. Further, the handle 520, includes fenestrations 522 which lighten the weight of the plate driver, and at the end of the handle, there is a buttressed area 525, which has a wider flat surface that can be used to tap the plate into the bone. FIGS. 32 and 33 illustrate a plate 600 being inserted into the cortical section of a calcaneus using the plate driver 500.

The screws useful with the plate of the present invention are self-starting, self-tapping screws including the option of partial or full cannulation. The screws include a cutting 142 end having multiple flutes 144, and preferably 2 or 3 flutes about a conical recess. The screws further include a partial taper 132 of the inner diameter in the proximal end over the first several thread turns, for example over 2-8, and preferably over 3-5 turns in order to increase the fatigue life of the screw as well as providing potential physiological advantages in use. The screws further include a torque driving recess. The screws 120, 140, 150 have a threaded distal end and a head including a torque driving recess 156. The head of the locking screw includes locking means, such as a variable locking mechanism 160, which could be a bushing that mates with the screw head so as to lock the screw relative to the plate at a desired angle, or could include external screw threads 134 that mate with internal threads in the locking screw hole at a pre-selected angle, in this instance, the screw axis is perpendicular to the longitudinal axis of the plate. The screw used in the compression slot has a rounded rear shoulder (such as a hemisphere, or a torroid) which mates with the concavely rounded groove of the compression slot so as to maximize surface contact between the screw head and the inclined geometry of the compression slot. The lateral edge of the compression slot further includes an inclined shoulder that slopes downward toward the bone-contacting surface of the plate and which is engaged by the screw head to cause the translation of the screw and attached bone fragment along the long axis of the slot and towards the locking hole.

The plate is formed of a biocompatible material, and preferably a metal such as surgical grade stainless steel, titanium or a titanium alloy or a cobalt chromium alloy. Preferably, the plate web has a thickness of between about 1.0 and about 2.5 millimeters, more preferably between about 1.5 and about 2 millimeters, and most preferably between about 1.5 and about 1.8 millimeters. The plate includes a raised continuous outer edge 16 which is defined between the top and the bottom surface and which has a total thickness of about 2 and 5 millimeters, or roughly twice the width of the web portion of the plate.

In addition, the plate can include a small through hole sized to receive a K-wire or other similar guide wire.

During the surgery the joints are first prepped which may include de-articulation between the bones to be fused and removal of any bone as part of the osteotomy, and as necessary, the plate is bent to contour to the bone surface. A pilot hole may be drilled into the bone into which the plate will be inserted. The plate is inserted into the plate recess in the plate driver and secured by tightening the plate upward in the plate holder using the plate holder having an end that has threads which mate with the locking threads of the locking hole in the plate. The plate is tamped into the cancellous portion of the bone fragment optionally by tapping the plate driver with a one pound mallet as is necessary to insert the plate. The plate should be driven until the recess or pocket makes contact with the anterior portion of the calcaneus. Once the plate is sunk, a drill guide is mated to the plate drive, and a hole is drilled for the locking screw. The plate can be held in position using olive wires (thru the non-locking hole and into the bone). The plate is located such that all of the screws are aimed into the targeted bones and away from the joint, fracture, or bone interface. The olive wire is removed if used, and a pilot hole is drilled at the end of the plate that includes the first hole and this hole is pinned or screwed. A second pilot hole may be drilled for the non-locking screw at the desired angle given an optional 15° of conical rotation within the non-locking hole and a non-locking screw is inserted into this pilot hole and tightened. As the screw is tightened in the angled hole, it will drive compression toward the fusion site and the first hole. The plate allows for up to 1.5 millimeters of compression.

Finally, a pilot hole is drilled in the cortical surface of the second bone fragment, for example using a drill guide such as a guide including keyway guides (i.e. lobes) that interlock with corresponding keyway openings in the locking screw hole and a locking screw is secured in this hole. The plate is viewed radiographically, and the soft tissues are closed in the usual manner.

This invention has been described in detail with reference to specific embodiments thereof, including the respective best modes for carrying out each embodiment. It shall be understood that these illustrations are by way of example and not by way of limitation.

What is claimed is:

1. A plate for bone fixation comprising:
    a first end providing a cutting edge;
    a tapered end which tapers from a lateral edge of the plate with a distal edge having a larger thickness to allow for a proximal portion of the plate to be driven into a bone;
    a bottom surface configured for contact with a bone;
    a top surface spaced-apart from the bottom surface, wherein an open-ended passageway communicates between the top surface and the bottom surface, the open-ended passageway being defined in offset relation to at least one of the top surface and the bottom surface, with a portion of the top surface circumferentially adjacent a top open-end of the passageway that is configured to receive a head of a screw within an angle of rotation of up to 20°; and
    a shroud extending outward from the top surface at an oblique angle and covering at least a portion of the top open-end, the shroud adapted to be interposed between a tissue and the head of the screw so as to prevent tissue irritation and provide compression to the bone.

2. The plate of claim 1, further comprising a compression slot passageway communicating between the top surface to the bottom surface.

3. The plate of claim 1, wherein an axis of the passageway forms an angle of between 25° and 35° with the top surface.

4. A plate for bone fixation comprising:
    a bottom surface configured for contact with a bone;
    a top surface arranged in spaced-relation to the bottom surface, wherein a first open-ended passageway is defined between the top surface and the bottom surface having a passageway axis and being sized to permit a screw to be inserted therethrough with an angle between a screw axis and the passageway axis to allow for a rotation of the screw about the passageway axis, the passageway configured to enclose a head of the screw wherein the passageway axis forms an angle with respect to the bottom surface between 10° and 45°; and
    an arcuate shroud projecting outwardly from the top surface at an oblique angle and covering at least a portion of an open-end of the passageway, the shroud adapted to be interposed between a tissue and the head of the screw.

5. The plate of claim 4, wherein the angle of the passageway axis with respect to the bottom surface is between 15° and 40°.

6. The plate of claim 4, the angle of the passageway axis with respect to the bottom surface is between 25° and 35°.

7. The plate of claim 4, further comprising a second open-ended passageway is defined through the plate that communicates between the top surface and the bottom surface.

8. The plate of claim 4, further comprising a tapered crescent-shaped cutting edge.

9. A plate system for use in associated bone comprising:
a screw having distal threads and a head having a surface without external threads;
a plate having a bottom surface configured for contact with a bone and a top surface with an open-ended passageway communicating between the top surface and the bottom surface, the open-ended passageway being defined in offset relation to at least one of the top surface and the bottom surface, with a portion of the top surface circumferentially adjacent a top open-end that is configured to receive the head of the screw at an angle wherein the passageway is shaped so as to permit the screw to be inserted therethrough with an angle between a screw axis and a passageway axis of up to 20°; and
a shroud projecting outwardly from the top surface covering at least a portion of the top open-end, the shroud adapted to minimize interaction between a tissue and the head of the screw.

10. The plate of claim 9, wherein the plate has a distal edge of the plate provides a shoulder so as to allow for a proximal portion of the plate to be driven into a bone.

11. The plate of claim 9, wherein an axis of the passageway forms an angle of between 10° and 45° with the top surface.

12. The plate of claim 9, wherein an axis of the passageway forms an angle of between 25° and 35° with the top surface.

13. The plate of claim 9, wherein a straight taper cutting edge is formed at an first end.

14. A plate system comprising:
a locking screw having distal threads and a head having external threads;
a non-locking screw having distal threads and a head having a rounded rear Shoulder surface; and
a plate having a top surface and a bottom surface that is configured to be in contact with the bone, the plate having a first tab and a second tab aligned along a longitudinal axis of the plate and joined by a middle section defining a first hole in communication with the bottom surface; wherein the first tab terminates in a cutting edge configured to cut bone upon application of a driving force to the plate; wherein the second tab includes a locking screw hole, wherein the first hole defines a screw hole axis that forms an angle with respect to the longitudinal axis of the plate, the first hole permitting variation of an axis of a screw when rotated about the axis of the first hole; and a shroud which is formed on and raised above the top surface of the plate in order to sufficiently support the screw when it is received in the first hole and to shroud the head of the non-locking screw so as to minimize the possibility of tissue irritation from the head of the non-locking screw.

15. The plate system as set forth in claim 14, wherein the screw axis of the non-locking screw within the first screw hole can be varied with respect to the screw hole axis by up to 15° of conical rotation.

16. The plate system as set forth in claim 14, wherein the shroud forms a portion of a cylinder.

17. The plate system as set forth in claim 14, wherein the system further includes a drill guide which interacts with the second hole to allow a pilot hole to be drilled in the associated bone at a desired angle.

18. The plate system as set forth in claim 17, further including a plate driver which includes a recess into which the plate is configured to be seated for insertion of the plate into the associated bone.

19. The plate system as set forth in claim 18, wherein the plate driver further includes a handle having a longitudinal axis that projects in a direction parallel to the longitudinal axis of the plate when the plate is seated in the recess.

20. The plate system as set forth in claim 19, wherein the plate driver further includes a plate holder portion which includes the recess and which is attached to the handle such that when the plate is seated in the recess, the longitudinal axis of the plate is offset by a distance from the longitudinal axis of the handle.

21. The plate system as set forth in claim 14, further including a drill and a drill guide, wherein the drill guide can be mounted from the plate driver to guide placement of the drill to drill an opening into the associated bone for the first hole of the plate.

* * * * *